US007822244B2

(12) United States Patent
Blumhofer

(10) Patent No.: US 7,822,244 B2
(45) Date of Patent: Oct. 26, 2010

(54) SEGMENTING MEDICAL IMAGE DATA SETS

(75) Inventor: Andreas Blumhofer, Neubiberg (DE)

(73) Assignee: BrainLAB AG, Feldkirchen (DE)

( * ) Notice: Subject to any disclaimer, the term of this patent is extended or adjusted under 35 U.S.C. 154(b) by 1066 days.

(21) Appl. No.: 11/534,869

(22) Filed: Sep. 25, 2006

(65) Prior Publication Data
US 2007/0076932 A1 Apr. 5, 2007

Related U.S. Application Data

(60) Provisional application No. 60/725,372, filed on Oct. 11, 2005.

(30) Foreign Application Priority Data
Sep. 23, 2005 (EP) .................................. 05020816

(51) Int. Cl.
*G06K 9/00* (2006.01)
(52) U.S. Cl. ....................... 382/128; 382/131; 382/132; 382/173; 382/284; 382/190; 600/423; 600/424
(58) Field of Classification Search ................. 382/128, 382/131, 132, 173, 284, 190, 294; 600/423, 600/424, 434; 128/920, 922
See application file for complete search history.

(56) References Cited
U.S. PATENT DOCUMENTS
2003/0210820 A1* 11/2003 Lachner et al. ............. 382/209

2005/0143651 A1* 6/2005 Verard et al. ................ 600/424
2006/0084867 A1* 4/2006 Tremblay et al. ........... 600/434
2006/0142983 A1* 6/2006 Sorensen et al. ............. 703/11
2008/0269596 A1* 10/2008 Revie et al. ................. 600/424

FOREIGN PATENT DOCUMENTS
EP 1 363 242 11/2003

OTHER PUBLICATIONS

Lilla Zöllei, "Piecewise Non-rigid Registration of 3D MR and CT Images of the Spine", Research Abstracts [Online] 2000, httb://www.ai.mit.edu.
Pitiot et al., "Piecewise Affine Registration of Biological Images", Biomedical Image Registration, 2$^{nd}$ International Workshop, 2003.

* cited by examiner

*Primary Examiner*—Samir A. Ahmed
*Assistant Examiner*—Ali Bayat
(74) *Attorney, Agent, or Firm*—Renner, Otto, Boisselle & Sklar, LLP

(57) ABSTRACT

A method for segmenting a body structure image data set produced from a medical imaging method includes: using a reference data set to define delineated body structures in the body structure image data set; and ascertaining an overall mapping function that substantially maps a reference data set onto the body structure image data set, wherein the overall mapping function comprises a portion that includes a dissection of the body structure image data set into structural parts and their individual rearrangement, and a portion which includes a global deformation and/or shift of the body structures.

10 Claims, 2 Drawing Sheets

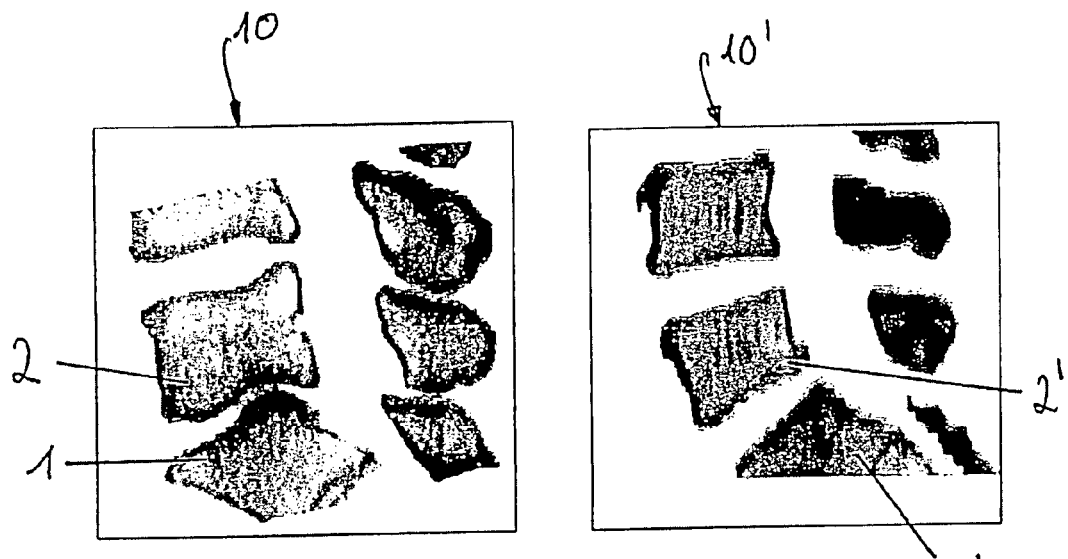
Figure 1
Figure 2
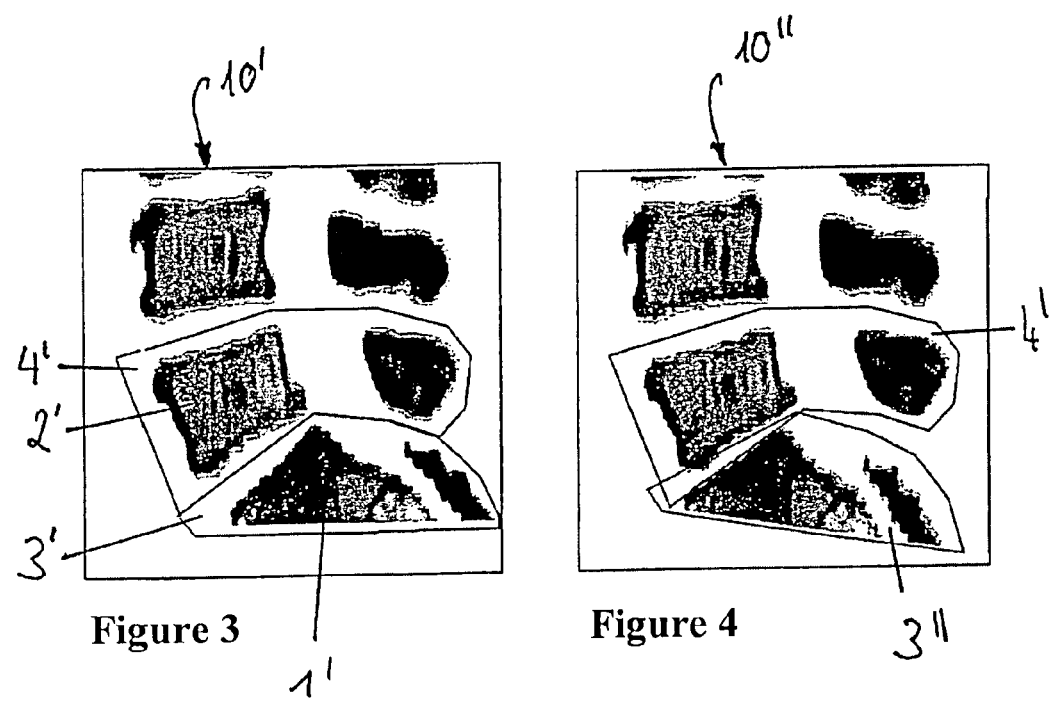
Figure 3
Figure 4

SEGMENTING MEDICAL IMAGE DATA SETS

RELATED APPLICATION DATA

This application claims priority of U.S. Provisional Application No. 60/725,372 filed on Oct. 11, 2005, which is incorporated herein by reference in its entirety.

FIELD OF THE INVENTION

The present invention relates to medical imaging and, more particularly, to segmenting data sets from medical imaging methods.

BACKGROUND OF THE INVENTION

Physicians now commonly enlist imaging methods that completely or partially detect internal body structures of a patient. These methods include, for example, computer tomography, nuclear spin (MR) tomography, PET and SPECT methods, and x-ray methods. The internal body structures detected by the imaging method, with the aid of a computer, can be output as sectional images or also as a three-dimensional reconstruction. Such an image output significantly aids the physician in analyzing and classifying the individual structures in the interior of the patient's body.

Sometimes, however, some of the cited methods are unable to exactly and/or completely delineate individual structures from each other. This can occur particularly when two different structures yield the same contrast value and/or color value. It is then not always possible, and also very expensive, to delineate such structures by means of another imaging method. As a result, reference atlases are then adduced which contain typical shapes of internal structures for particular parts of the body as they would appear in particular imaging methods.

If, for example, a portion of the delineation of a certain body structure from the imaging method with respect to its surroundings is already available, but another portion is not, then a mapping function can be ascertained from the available portion of the delineation in the body structure image data set and a corresponding portion of a reference data set (e.g., the atlas). The mapping function can map the corresponding parts of the reference data set onto the parts of the body structure image data set. If this mapping function is then available, then the delineations and/or physical features that cannot be gathered directly from the body structure image data set can be obtained from the reference data set, e.g., by applying the mapping function to the reference data set. EP 1 363 242 A1 describes such a method, in which a mapped reference label data set is also used to generate an individualized label data set by superimposing it with the patient data set.

The mappings used in such methods include global elastic deformation (e.g., an entire body structure, even if it consists of individual parts, is elastically deformed as a reference data set, such that it is adapted to the actual body structure image data set). The resulting match, for example, then can be used to delineate and visually highlight structures in the body structure image data set (patient data set). This process also is referred to as segmenting, or, because reference data set atlases are used, "atlas segmenting" or "atlas segmentation". This atlas segmenting, when mapping, also can take into account global shifts in the entire structure.

In some applications, however, such a procedure as described above has not been successful. This is particularly true where structures comprise a number of separate constituents. In such instances, segmenting may be unstable or it may not work at all.

SUMMARY OF THE INVENTION

The present invention provides a novel system and method for mapping a reference data set, such as an atlas data set, onto a patient data set to enhance delineations and/or physical features in the patient data set. Instead of mapping an entire data set which consists of several parts of the body, the patient data set is separated into regions, including in particular regions corresponding to respective structural parts of the patient's body, such that they can be individually rearranged, whereby any twisting and/or shifting of such parts of the patient's body relative to the corresponding parts in the patient data set, can be accommodated.

Accordingly, the invention provides a segmenting method for a body structure image data set (patient data set) produced using a medical imaging method, the method comprising the steps of:

providing a reference data set which can be assigned to the body structure image data set;

ascertaining an overall mapping function which substantially maps the reference data set onto the body structure image data set; and defining delineated body structure data in the body structure data set by means of the mapped reference data set; and wherein the overall mapping function includes a portion which includes the dissection of the body structure into structural parts and their individual rearrangement, and a portion which includes the global deformation and/or shift of the body structure.

In other words, the reference data set can be separated into a number of regions and/or parts that can be moved independently of each other. An advantage of this procedure is that body structure image data sets can be segmented, even when segmentation is not possible using previous methods (e.g., due to individual parts being significantly twisted and/or shifted with respect to each other). By dissecting the body structure into structural parts, a discontinuous deformation (segmenting) is provided as opposed to the purely continuous deformation that has previously been used. It may also be said that discontinuously deformed structures can be localized and/or segmented.

As used herein, discontinuous deformation refers to applying a specific function (e.g., a twisting or moving function) to only a portion of the data set (e.g., to a segment of the reference data set), without applying the function to other portions of the data set. In other words, the data set is segmented into separate pieces or groups, and then the separate pieces are moved, preferably in a rigid manner, relative to other pieces or groups.

The cited individual rearrangement of the structural parts can include individually rotating structural parts relative to each other, or also individually shifting structural parts relative to each other. It also can include both.

The overall mapping function portion, which comprises the dissection of the body structure into structural parts and their individual rearrangement, may be ascertained before the other overall mapping function portion (e.g., before ascertaining the global deformation and/or shift of the body structure).

In another configuration, the two portions of the overall mapping function can be ascertained together. Further, the global deformation portion can be implemented in advance. It also is conceivable for these function portions to be ascertained independently via different methods, until the overall mapping function is ascertained.

It also is contemplated to first use one of the two portions of the overall mapping function on its own and, if it is established that a result and/or a stable result is not obtainable using a single portion, then to add the other portion. Such a case can use global deformation, then establish that a result and/or a stable result cannot be achieved, and then use individual part dissection and rearrangement of the parts.

The overall mapping function portion, which comprises the dissection of the body structure into structural parts and their individual rearrangement ("individual portion"), may take ancillary conditions into account that are predetermined by the anatomy of the body structure and its relationship to surrounding body structures. For example, when segmenting the femoral bone or surrounding structural parts, it may be advantageous to take into account that this bone only can be moved in a particular way point axes). In this way, very stable segmentations can be obtained. Further, the ancillary conditions can include anatomically possible axes of rotation and/or joint axes or anatomically compliant changes in the distance of body structures or groups and/or parts of the same.

In very general terms, segmenting is suitable for all body structures, and in particular also for body structure image data sets which include bone structures or groups and/or parts of the same.

According to another aspect of the invention, there is provided a program which, when it is running on a computer or is loaded onto a computer, causes the computer to perform a method as described above, and to a computer program storage medium comprising such a program.

According to a further aspect of the invention, a device for segmenting a body structure image data set produced using a medical imaging method comprises: a data input device for inputting the body structure image data set and a reference data set assignable to the body structure image data set; a memory for storing the data sets; and a computational device, by means of which an overall mapping function is ascertained which substantially maps the reference data set onto the body structure image data set, wherein delineated body structures are defined in the body structure data set by means of the mapped reference data set, wherein the overall mapping function includes a portion which includes the dissection of the body structure into structural parts and their individual rearrangement, and a portion which includes the global deformation and/or shift of the body structure. The device can be fitted with means for performing the methods explained herein, such as, for example, computer-aided medical planning and visualizing systems.

BRIEF DESCRIPTION OF THE DRAWINGS

The forgoing and other features of the invention are hereinafter discussed with reference to the drawings, wherein:

FIG. 1 is an image of an exemplary body structure image data set (patient data set);

FIG. 2 is an image from an exemplary reference data set (reference atlas) which can be assigned to the image from FIG. 1 in accordance with the invention;

FIG. 3 is an exemplary reference data set image in which structural parts have been delineated in accordance with the invention;

FIG. 4 is the exemplary reference data set image of FIG. 3, with the structural parts shifted/twisted in accordance with the invention.

DETAILED DESCRIPTION

Figure 5:
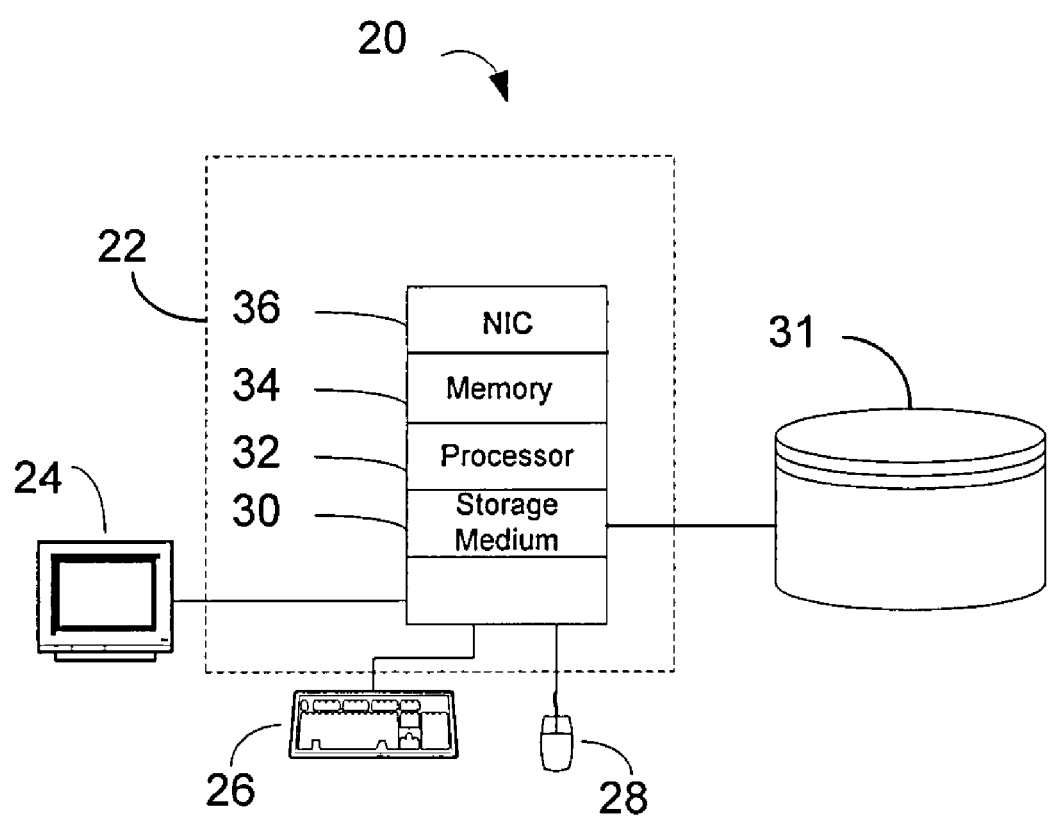
FIG. 5 is a block diagram of an exemplary computer system that may be used to implement one or more methods in accordance with the invention.

As described herein, segmenting is made possible even in cases in which conventional means fail. An example of such a case is shown in FIGS. 1 and 2, each of which illustrate exemplary vertebral structures 10, 10'. FIG. 1 is an actual CT recording of a patient's vertebral structure 10, while FIG. 2 is an exemplary reference data set or "atlas" vertebral structure 10'. As can be seen in FIG. 1, the structure 10 includes a number of vertebrae, wherein vertebra 1 is significantly shifted towards and twisted relative to vertebra 2. This twist and/or shift can be ascertained relative to the vertebrae in reference data set of FIG. 2. In the reference data set of FIG. 2, a separation between the vertebrae 1', 2' is larger than the separation between vertebrae 1, 2 of FIG. 1. Further, the vertebrae 1', 2' are not twisted with respect to each other to the same degree as the vertebrae 1, 2 of FIG. 1.

A mapping function for mapping the reference structure 10' onto the patient structure 10, wherein the mapping function is based only on deformations or shifts of the entire structure 10', cannot be found. Continuous deformation in accordance with the prior art cannot achieve a reduction in distance between the two lower vertebrae or the lateral misalignment, e.g., the shift and rotation.

In addition, there often are other difficulties associated with reference atlases generated for a particular situation (e.g., a particular patient), since mutations or variations are not necessarily pathological. For example, rotations between the hip and thigh occur naturally and, thus, only in rare cases will a patient's leg have the same position in the patient CT data sets as in the reference data set (atlas).

The present invention provides a system and method that can act both in the former pathological cases and in the non-pathological cases, and thus enable reliable segmentation (or also localization) of the body structures. More specifically, separations between vertebra can be made in the reference data set 10' as shown in FIG. 3, e.g., the reference data set can be sub-divided and/or dissected into known regions which surround the problematic structures. FIG. 3 shows the region and/or structural part 3' which contains the vertebra 1', and the region and/or structural part 4' which includes the vertebra 2', wherein the structural part 3' is different from and delineated from the structural part 4'. It is then possible to shift and/or rotate structural parts 3', 4' until they approximate and/or assimilate to the topology of the patient data set 10.

Such an image, in which the region 3' has been rotated and/or shifted until it superimposes the region 4', is shown in FIG. 4. The position of the structural part 3' has now transitioned to the state 3" which comes much closer to the state in FIG. 1 (patient CT). From this state, segmenting now can be achieved using a conventional deformation function, stably and within a relative short period of time.

Once the suitable overall mapping function has been ascertained in this way, it is relatively simple to segment surrounding structures and/or structural parts, because the mapping function can be used again. The physician can therefore be provided with a segmented representation of particular body structures (vertebra or group of vertebrae or also soft tissues such as the brain stem) within a relative short period of time.

It also is noted that it is possible to use an individual reference bone that would have to be adapted to the body structure image data set. At least purely elastic deforming (elastic fusion and/or elastic matching) encounters problems here, because adjacent bones in the reference data set do not comprise corresponding bone parts and the system would still try to adapt them to the individual bones. Furthermore, reference should also be made to the fact that overlapping individual structural parts (for example parts 3" and 4" in FIG. 4) generates regions in which a number of items of information about a region are available, while on the other hand, regions are available about which there is no information. This can easily be solved by using a maximum value where a number of items of information are available, and filling empty regions with zero values. Reference should also be made to the fact that using a reference label data set and mapping the data set onto an individualized label data set, as described in EP 1 363 242 A1, can also be incorporated within the framework of the present invention.

Methods and systems according to the invention may also have specific application in the field of segmenting for CT-based spine applications, hip applications and knee applications.

FIG. 5 is a block diagram of a system 20 for implementing one or more of the methods described herein. The system 20 includes a computer 22 for processing data, and a display 24 for viewing system information. The technology used in the display is not critical and may be any type currently available, such as a flat panel liquid crystal display (LCD) or a cathode ray tube (CRT) display, or any display subsequently developed. A keyboard 26 and pointing device 28 may be used for data entry, data display, screen navigation, etc. The keyboard 26 and pointing device 28 may be separate from the computer 22 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 26 and pointing device 28. Touch screens may be beneficial when the available space for a keyboard 26 and/or a pointing device 28 is limited.

Included in the computer 32 is a storage medium 30 for storing information, such as application data, screen information, programs, etc., which may be in the form of a database 31. The storage medium 30 may be a hard drive, for example. A processor 32, such as an AMD Athlon 64® processor or an Intel Pentium IV® processor, combined with a memory 34 and the storage medium 30 execute programs to perform various functions, such as data entry, numerical calculations, screen display, system setup, etc. A network interface card (NIC) 36 allows the computer 22 to communicate with devices external to the system 20.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for segmenting a body structure image data set produced from a medical imaging method, comprising:
    using a reference data set to define delineated body structures corresponding to the body structure image data set; and
    ascertaining an overall mapping function that substantially maps the reference data set onto the body structure image data set, wherein the overall mapping function comprises
        a portion that includes a dissection of the reference data set into a plurality of structural parts and the individual rearrangement of at least one structural part of the plurality of structural parts relative to at least one other structural part of the plurality of structural parts of the reference data set, and
        a portion that includes a mapping function that maps the dissected and rearranged plurality of parts onto corresponding parts of the body structure image data set.

2. The segmenting method according to claim 1, wherein the individual rearrangement includes individually rotating structural parts relative to each other.

3. The segmenting method according to claim 1, wherein the individual rearrangement includes individually shifting structural parts relative to each other.

4. The segmenting method according to claim 1, wherein using includes ascertaining the structural parts and their individual rearrangement before ascertaining the mapping function that maps the dissected and rearranged parts onto the corresponding parts of the body structure image data set.

5. The segmenting method according to claim 1, wherein using includes ascertaining the structural parts and their individual rearrangement together with ascertaining the mapping function that maps the dissected and rearranged parts onto the corresponding parts of the body structure image data set.

6. The segmenting method according to claim 1, wherein using includes taking into account ancillary conditions which are predetermined by the anatomy of the body structure and its relationship to surrounding body structures.

7. The segmenting method according to claim 6, wherein the ancillary conditions include at least one of anatomically possible axes of rotation, joint axes, changes in the distance of body structures, or groups and/or parts of the same.

8. The segmenting method according to claim 1, wherein the body structure image data set includes at least parts of bone structures and/or bone groups.

9. A computer program embodied on a non-transitory computer readable medium for segmenting a body structure image data set produced from a medical imaging method, comprising:
    code that uses a reference data set to define delineated body structures in the body structure image data set; and
    code that ascertains an overall mapping function that substantially maps the reference data set onto the body structure image data set, wherein the overall mapping function comprises
        a portion that includes a dissection of the reference data set into a plurality of structural parts and the individual rearrangement of at least one structural part of the plurality of structural parts relative to at least one other structural part of the plurality of structural parts of the reference data set, and a portion that includes a mapping function that maps the dissected and rearranged plurality of parts onto corresponding parts of the body structure image data set.

10. A device for segmenting a body structure image data set produced using a medical imaging method, comprising:

a processor;

a data input device for inputting the body structure image data set and a reference data set assignable to the body structure image data set;

a memory for storing the data sets;

segmentation logic stored in memory and executable by the processor, the segmentation logic comprising logic that uses the reference data set to define delineated body structures in the body structure image data set; and logic that ascertains an overall mapping function that substantially maps a reference data set onto the body structure image data set, wherein the overall mapping function comprises a portion that includes a dissection of the reference data set into a plurality of structural parts and the individual rearrangement of at least one structural part of the plurality of structural parts relative to at least one other structural part of the plurality of structural parts of the reference data set, and a portion that includes a mapping function that maps the dissected and rearranged plurality of parts onto corresponding parts of the body structure image data set.

* * * * *